United States Patent [19]

Scherer, Jr. et al.

[11] Patent Number: 5,214,214

[45] Date of Patent: May 25, 1993

[54] PERFLUORO BRANCHED ALKYL ETHERS AND EMULSIONS

[75] Inventors: Kirby V. Scherer, Jr., Santa Monica, Calif.; Kouichi Yamanouchi, Sakai, Japan; Kazumasa Yokoyama, Toyonaka, Japan

[73] Assignee: The Green Cross Corporation, Osaka, Japan

[21] Appl. No.: 860,567

[22] Filed: Mar. 30, 1992

Related U.S. Application Data

[60] Continuation of Ser. No. 425,031, Oct. 23, 1989, abandoned, which is a division of Ser. No. 582,448, Feb. 22, 1984, Pat. No. 4,943,595, which is a continuation-in-part of Ser. No. 300,273, Sep. 8, 1981, abandoned.

[51] Int. Cl.$^5$ .................. C07C 43/12; C07C 211/00; A61K 31/08; A61K 31/12
[52] U.S. Cl. ................... 564/510; 564/496; 568/604; 568/615; 568/677; 568/683; 568/685
[58] Field of Search .............. 564/510; 514/832, 672

[56] References Cited

U.S. PATENT DOCUMENTS

2,623,096 12/1952 Robinson ............ 568/685
3,952,439 8/1976 Yokoyama ........... 514/722
4,366,169 12/1982 White ............... 514/672

OTHER PUBLICATIONS

Haszeldine, "Perfluoro amines", Chem. Abstr. (45) 1505 (1951) Research 3, 430–1 (1950).
Plashkin et al., "Electrochemical fluorination etc", Chem. Abst., vol. 80 (1974), p. 379 Abst. No. 108098b Zh. Org. Khin. 1973, 9(12), 2525–31.
Cao et al, "Quantitative analysis of fluorocarbon compound", Chem. Abst. vol. 95, (1981), pp. 436–7 Abst. No. 95:175875c, Yu Chi Wua Hsuch (1981) 4, 267–72.

Primary Examiner—Allen J. Robinson
Assistant Examiner—P. O'Sullivan
Attorney, Agent, or Firm—Cushman, Darby & Cushman

[57] ABSTRACT

There is provided a novel perfluorochemical represented by the formula,

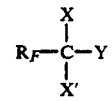

wherein $R_F$ is a perfluoroalkyl group, a perfluoro alkoxyalkyl group or a perfluoroalkyloxy group, X and X' are same as or different from each other and are a fluorine atom or a perfluoroalkyl group, and Y is a perfluoroalkyloxy group or a perfluoro dialkylamino group, the total number of the carbon atoms contained being an integer of 8 to 11 inclusive. The perfluorochemical is prepared by perfluorinating the corresponding partially fluorinated compound which may have unsaturated hydrocarbon moiety, only with molecular fluorine in a stoichiometric excess amount in an inert solvent.

The perfluorochemical is used for preparing a stable emulsion as blood substitutes or perfusion media.

2 Claims, No Drawings

PERFLUORO BRANCHED ALKYL ETHERS AND EMULSIONS

This is a continuation of application Ser. No. 07/425,031, filed on Oct. 23, 1989, which was abandoned upon the filing hereof which is a divisional of application Ser. No. 06/582,448, filed Feb. 22, 1984 U.S. Pat. No. 4,943,595; which is a continuation-in-part of application Ser. No. 06/300,273, filed Sep. 8, 1981 now abandoned.

BACKGROUND OF THE INVENTION

1. Field of the Invention

The present invention relates to novel perfluorochemicals, and to their synthesis by the method of direct liquid-phase fluorination with undiluted $F_2$.

2. Description of the Prior Art

The use of perfluorochemical emulsions as blood substitutes has received intensive study since the pioneering experiments of Clark and Geyer. At this time, a commercially available perfluorochemical emulsion is being used in humans under limited official or government permission in the medical field in Japan and in the U.S.A.

An appropriate perfluorochemical for blood substitutes must be non-toxic and metabolically inert, must dissolve as much oxygen as possible, and must be eliminated from the body when it is no longer needed medically, preferably at least 90% within one month.

A major factor in elimination rate is vapor pressure, but vapor pressure is not the whole story, because it is reported that perfluoro-cis-decalin (b.p. 143° C., vapor pressure at 37° C.; 10.1 mmHg) has a slightly higher elimination rate than the trans isomer (b.p. 141° C., vapor pressure at 37° C.; 11.6 mmHg), though a slightly lower vapor pressure. Furthermore, it is found that the perfluorochemicals having hetero atoms, such as N and/or O, have much slower elimination rates that perfluoro hydrocarbon analogues of similar molecular weight, even if they have an appropriate vapor pressure. It is more likely that the elimination rate of perfluorochemicals, at least the $C_9$–$C_{11}$ perfluorochemicals which are the most useful for blood substitutes, depends strongly on their chemical structure rather than boiling point and vapor pressure. For example, the elimination rate order in the following perfluorochemicals is $IV>>III\geqq I>II$, even though their vapor pressures and b.p.'s are in extremely narrow range.

Nichka discloses in DT-OS 2253534 as the solvent of oxygen perfluoroisopropyl n-hexyl ether of the formula

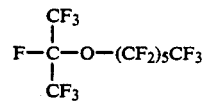

Apparently the data so far obtained do not reveal the relationship between chemical structure and elimination rate, probably owing to the limited range of perfluorochemical structures so far tested.

The second point is the problem of toxicity which causes pulmony emphysema. Perfluorochemicals having a lower vapor pressure have generally this toxicity due to the fast elimination from the body through the lung. The elimination burdens the lung and causes the pulmonary emphysema.

The third point is stability of the emulsion of perfluorochemicals. The emulsion having particles of which size is less than $0.3\mu$, preferably less than $0.2\mu$ must be stable under sterilizing heat and also during long time storage.

The principle industrial processes now employed in perfluorochemical synthesis, namely electrochemical fluorination or cobalt trifluoride fluorination are not suitable for the fluorination of sensitive compounds, for example, highly branched compounds or structurally strained compounds, because considerable carbon-skeleton rearrangement and/or breakdown of the carbon skeleton often occurs during the reaction, resulting not in pure substances but mixtures of isomeric compounds containing impurities and incompletely fluorinated compounds. In addition to these principal routes to perfluorochemicals, one other is worth mentioning: The direct fluorination of solid starting materials using elemental $F_2$ and a diluent such as $N_2$ or He is very general and powerful laboratory synthesis of a wide variety of perfluorochemicals, including cyclic and branched hydrocarbons and ethers. Unfortunately, this method is impractical for commercial use. The inherently slow mass transfer through solids at low temperature makes it unlikely that the process can be economically scaled up, and even the published laboratory synthesis of low molecular weight products involves many days of reaction time to produce only a few grams of product.

| I | II | III | IV |
|---|---|---|---|
| 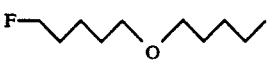 | 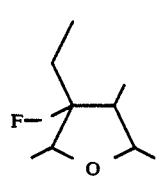 | 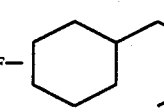 | 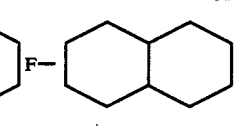 |
| $C_{10}F_{22}O$ (554) | $C_{10}F_{20}O$ (516) | $C_{10}F_{20}$ (500) | $C_{10}F_{18}$ (462) |
| b.p. 136–137° C. | 144–145° C. | 144–145° C. | 141–142° C. |
| vapor pressure at 37° C.: | | | |
| 11.8 mmHG | 11.7 mmHg | 12.5 mmHg | 12.7 mmHg |

In formulae shown herein, "F-" means that the compound is perfluorinated, unless otherwise stated.

SUMMARY OF THE INVENTION

In accordance with the present invention, there are provided novel perfluorochemicals which are ether and tert-amine derivatives of perfluorocarbons and are useful as synthetic blood substitutes or perfusion media.

The perfluorochemical is represented by the formula, $$R_F-\underset{\underset{X'}{|}}{\overset{\overset{X}{|}}{C}}-Y \quad [I]$$

wherein $R_F$ is a perfluoroalkyl group, a perfluoro alkoxyalkyl group or a perfluoroalkyloxy group, X and X' are same as or different from each other and are a fluorine atom or a perfluoroalkyl group, and Y is a perfluoroalkoxy group or a perfluoro dialkylamino group, the total number of the carbon atoms contained being an integer of 8 to 11 inclusive.

In an aspect of the present invention, there is provided a perfluoroalkyl ether derivative of the formula, $$R_{F1}-\underset{\underset{X_2}{|}}{\overset{\overset{X_1}{|}}{C}}-O-R_{F2} \quad [II]$$

wherein $R_{F1}$ is a $C_1$-$C_9$ perfluoroalky group, a perfluoro $C_1$-$C_2$ alkoxy-$C_1$-$C_3$-alkyl group or a perfluoro $C_1$-$C_5$ alkyloxy group, $X_1$ and $X_2$ are same as or different from each other and are a fluorine atoms or a $C_1$-$C_3$ perfluoroalkyl group, and $R_{F2}$ is a $C_1$-$C_5$ perfluoroalkyl group, the total number of the carbon atoms contained being 8 to 11 inclusive.

Another aspect of the invention is to provide a perfluoroalkyl tertiary amine derivative of the formula, $$R_{F3}-\underset{\underset{X_4}{|}}{\overset{\overset{X_3}{|}}{C}}-N\underset{R_{F5}}{\overset{R_{F4}}{\diagup\diagdown}} \quad [III]$$

wherein $R_{F3}$ is a $C_1$-$C_6$ perfluoroalkyl group, $R_{F4}$ and $R_{F5}$ are same as or different from each other and are a $C_1$-$C_4$ perfluoroalkyl group, and $X_3$ and $X_4$ are same as or different from each other and are a fluorine atom or $C_1$-$C_3$ perfluoroalkyl group, the total number of the carbon atoms being an integer of $C_8$-$C_{11}$ inclusive.

Broadly speaking, the present invention provides a process for preparing perfluoroalkyl ethers or tert-amines by reacting the corresponding partially fluorinated compound with an excess amount of undiluted $F_2$ in a liquid phase consisting of an inert solvent and/or the perfluorinated product itself.

The perfluoroalkyl ether derivative or perfluoroalkyl tertiary amine derivative of the formula [I] can be prepared by reacting a partially fluorinated compound of the formula, $$R_{F1}'\quad \underset{\underset{X_2'}{|}}{\overset{\overset{X_1'}{|}}{C}}-Y_1 \quad [IV]$$

wherein $R_{F1}'$ is a perfluoroalkyl group, a partially fluorinated alkyl group, and an alkoxy group, a partially fluorinated alkyloxy group, an alkyloxyperfluoroalkenyl group, a partially fluorinated alkylidene group or a perfluoro isoalkylidene group; $X_1'$ and $X_2'$ are same as or different from each other and are a hydrogen atom, a fluorine atom or a perfluoroalkyl group; one of $X_1'$ and $X_2'$ being lacking when $R_{F1}'$ is a partially fluorinated alkylidene group or a perfluoroisoalkylidene group with a double bond between the $R_{F1}'$ and the carbon atom to which $R_{F1}'$ is connected; and $Y_1$ is an alkyloxy group or dialkylamino group; the total number of the carbon atoms contained being an integer of 8 to 11 inclusive; with molecular fluorine in an inert solvent at a temperature of $-75°$ C. to $100°$ C., the reaction being carried out so that molecular fluorine is maintained in stoichiometric excess during the reaction.

The present invention provides also new compounds among the starting partially fluorinated compounds of the formula [IV].

BRIEF DESCRIPTION OF THE DRAWING

One typical reaction system used in the present invention is shown in the accompanying drawing. There is a reaction chamber 1. It comprises a copper tube equipped with a copper or monel condenser 2 cooled by a Dry Ice-solvent sludge and used to minimize evaporation of products and solvent. A gas flow meter 3 is used to measure the fluorine flow. The micro-metering pump 4 is used to charge the starting materials to be perfluorinated. In the reaction chamber 1 there is provided UV lamp 5 with fused sapphire windows. A nitrogen purge line 6 is provided to prevent moisture and oxygen from diffusing back into the reactor. There is provided an efflux pipe 7 for unreacted $F_2$ and produced HF. On a commercial scale, the $F_2$ will be cycled and the HF will be electrolyzed in a standard fluorine cell (not shown). A stirring device 8 is provided in the reaction chamber 1. An external bath 9 for regulating the reactor temperature is provided surrounding the reaction chamber 1. A drain pipe 10 for sampling and collecting product is at the bottom of the chamber 1.

DETAILED DESCRIPTION OF INVENTION

The perfluorochemicals of the invention have high oxygen solubility, and a vapor pressure which is just about right for elimination from the human body without adverse effects thereon. The emulsions prepared from the perfluoro derivatives thereof possess high stability and low body tissue retention.

The perfluorochemical of the invention is a perfluoroalkyl ether or tertiary amine having 8-11 carbon atoms, whose chains are preferably branched or whose hetero atoms are preferably surrounded by at least one branched chain in both the perfluoroalkyl ether and perfluoro tert-amine cases.

By the term "branched" is meant a perfluorinated compounds whose chain structure has at least one secondary and/or tertiary carbon, preferably with the branched carbon attached to the hetero atom in both cases of perfluorinated ether and perfluorinated tert-amine.

This invention thus provides, for example, the following perfluorinated ether or tert-amine derivatives of $C_8$-$C_{11}$ compounds preferably having branched skeletons. I. Perfluorinated ether (1) Perfluoro-3-n-propoxy-2-methylpentane,
(2) Perfluoro-3-isopropoxy-2-methylpentane,
(3) Perfluoro-3-n-butoxy-2-methylpentane,
(4) Perfluoro-3-isobutoxy-2-methylpentane, (5) Perfluoro-3-sec-butoxy-2-methylpentane,
(6) Perfluoro-3-isopentoxy-2-methylpentane,
(7) Perfluoro-3-ethoxy-2,4-dimethylpentane,
(8) Perfluoro-3-prooxy-2,4-dimethylpentane,
(9) Perfluoro-3-isopropoxy-2,4-dimethylpentane,
(10) Perfluoro-3-n-butoxy-2,4-dimethylpentane,
(11) Perfluoro-3-isobutoxy-2,4-dimethylpentane,
(12) Perfluoro-2-n-propoxy-2-methylpentane,
(13) Perfluoro-2-isopropoxy-2-methylpentane,
(14) Perfluoro-2-n-butoxy-2-methylpentane,
(15) Perfluoro-2-isobutoxy-2-methylpentane,
(16) Perfluoro-2-sec-butoxy-2-methylpentane,
(17) Perfluoro-2-isopentoxy-2-methylpentane,
(18) Perfluoro-1-ethoxyheptane,
(19) Perfluoro-1-n-propoxyheptane,
(20) Perfluoro-1-isopropoxyheptane,
(21) Perfluoro-1-n-butoxyheptane,
(22) Perfluoro-1-isobutoxyheptane,
(23) Perfluoro-1-sec-butoxyheptane,
(24) Perfluoro-2-methoxy-4-ethyl-4-methylhexane,
(25) Perfluoro-2-ethoxy-4-ethyl-4-methylhexane,
(26) Perfluoro-2-methoxy-3-isopropyl-4-methylhexane,
(27) Perfluoro-2-ethoxy-3-isopropyl-4-methylhexane,
(28) Perfluoro-1,3-dimethoxy-2-methylpentane,
(29) Perfluoro-1,3-diethoxy-2-methylpentane,
(30) Perfluoro-2-pentoxy-2-methoxypropane,
(31) Perfluoro-2-pentoxy-2-ethoxypropane, and
(32) Perfluoro-2,2-dipropoxypropane, II. Perfluorinated tert-amine
(33) Perfluoro-1-dimethylamino-2-methylpentane,
(34) Perfluoro-1-ethylmethylamino-2-methylpentane,
(35) Perfluoro-1-diethylamino-2-methylpentane,
(36) Perfluoro-1-dimethylamino-2,4-dimethylpentane,
(37) Perfluoro-1-ethylmethylamino-2,4-dimethylpentane,
(38) Perfluoro-2-dimethylamino-2-methylpentane,
(39) Perfluoro-2-methylethylamino-2-methylpentane,
(40) Perfluoro-2-methypropylamino-2-methylpentane,
(41) Perfluoro-1-dimethylamino-2,2-dimethylpentane,
(42) Perfluoro-3-dimethylamino-2-methylpentane,
(43) Perfluoro-3-diethylamino-2-methylpentane,
(44) Perfluoro-3-dimethylamino-2,4-dimethylpentane, and the like.

Among the perfluoroalkyl ethers, preferable ones are those having a carbon number of 10 or 11 in molecule due to their vapor pressure sufficiently high to minimize the pulmonary emphysema, and to rendering more stable emulsion.

Also those having a straight chain structure are not preferable due to their slow elimination property and insufficient for rendering more stable emulsion. It is believed that the more the branched chain the better is. Thus, the ethers of the formula [II] in which $R_{F1}$ and $R_{F2}$ are simultaneously straight chain perfluoroalkyl groups and both $X_1$ and $X_2$ are fluorine atom, are inferior to the others in the properties. Further the ethers having perfluoromethyl ether linkage in any position of the molecule are inferior in emulsion stability as compared with the others.

Thus the more desirable perfluoroalkyl ether derivatives are represented by the formula [II], wherein $R_{F1}$ is a $C_1-C_8$ perfluoroalkyl group, a perfluoro $C_2$-alkoxy-$C_1-C_3$-alkyl group or a perfluoro $C_2-C_5$ alkoxy group, $X_1$ is a fluorine atom or a $C_1-C_3$ perfluoroalkyl group, $X_2$ is a $C_1-C_3$ perfluoroalkyl group, and $R_{F2}$ is a perfluoro $C_2-C_5$ alkyl group; the total number of the carbon atoms contained being 10 or 11.

And also, this invention provides the intermediate partially fluorinated derivatives of $C_8-C_{11}$ compounds which are the starting materials of the present process, such as:
(1) 3-n-Propoxy-undecafluoro-2-methyl-2-pentene,
(2) 3-Isopropoxy-undecafluoro-2-methyl-2-pentene,
(3) 3-n-Butoxy-undecafluoro-2-methyl-2-pentene,
(4) 3-Isobutoxy-undecafluoro-2-methyl-2-pentene,
(5) 3-sec-Butoxy-undecafluoro-2-methyl-2-pentene,
(6) 3-Isopentoxy-undecafluoro-2-methyl-2-pentene,
(7) 3-Ethoxy-tridecafluoro-2,4-dimethyl-2-pentene
(8) 3-n-Propoxy-tridecafluoro-2,4-dimethyl-2-pentene
(9) 3-Isopropoxy-tridecafluoro-2,4-dimethyl-2-pentene
(10) 3-n-Butoxy-tridecafluoro-2,4-dimethyl-2-pentene
(11) 3-Isopentoxy-tridecafluoro-2,4-dimethyl-2-pentene
(12) 2-n-Propoxy-tridecafluoro-2-methylpentane
(13) 2-Isopropoxy-tridecafluoro-2-methylpentane
(14) 2-n-Butoxy-tridecafluoro-2-methylpentane
(15) 2-Isobutoxy-tridecafluoro-2-methylpentane
(16) 2-sec-Butoxy-tridecafluoro-2-methylpentane
(17) 2-Isopentoxy-tridecafluoro-2-methylpentane
(18) 1-Isopropoxy-1H,1H,7H-dodecafluoroheptane
(19) 1-Ethoxy-1H,1H,7H-dodecafluoroheptane
(20) 1-n-Propoxy-1H,1H,7H-dodecafluoroheptane
(21) 1-Butoxy-1H,1H,7H-dodecafluoroheptane
(22) 1-Isobutoxy-1H,1H,7H-dodecafluoroheptane
(23) 1-sec-Butoxy-1H,1H,7H-dodecafluoroheptane
(24) 2-Methoxy-3H-hexadecafluoro-4-ethyl-4-methyl-2-hexene
(25) 2-Ethoxy-3H-hexadecafluoro-4-ethyl-4-methyl-2-hexene
(26) 2-Methoxy-hexadecafluoro-3-isopropyl-4-methyl-2-pentene
(27) 2-Ethoxy-hexadecafluoro-3-isopropyl-4-methyl-2-pentene
(28) 1,3-Dimethoxy-decafluoro-2-methyl-1-pentene
(29) 1,3-Diethoxy-decafluoro-2-methyl-1-pentene
(30) 2-Methoxy-2-(1H,1H,5H-octafluoropentoxy)-hexafluoropropane
(31) 2-Ethoxy-2-(1H,1H,5H-octafluoropentoxy)-hexafluoropropane
(32) 2,2-Dipropoxy-hexafluoropropane
(33) 1-Dimethylamino-undecafluoro-2-methyl-1-pentene
(34) 1-Ethylmethylamino-undecafluoro-2-methyl-1-pentene
(35) 1-Diethylamino-undecafluoro-2-methyl-1-pentene
(36) 1-Dimethylamino-tridecafluoro-2,4-dimethyl-1-pentene
(37) 1-Ethylmethylamino-tridecafluoro-2,4-dimethyl-1-pentene
(38) 2-Dimethylamino-tridecafluoro-2-methyl-pentane
(39) 2-Ethylmethylamino-tridecafluoro-2-methyl-pentane
(40) 2-Methylpropylamino-tridecafluoro-2-methyl-pentane
(41) 1-Dimethylamino-1H,1H-tridecafluoro-2,2-dimethylpentane
(42) 3-Dimethylamino-undecafluoro-2-methyl-2-pentene
(43) 3-Diethylamino-undecafluoro-2-methyl-2-pentene
(44) 3-Dimethylamino-tridecafluoro-2,4-dimethyl-2-pentene.

Among the above-mentioned compounds, the compounds No's. 12, 13, 14, 27, 28, 29 and 35 are already known and are excluded from the present invention.

It should be noted that even though $C_8$ perfluorochemicals may not be suitable as the only perfluorochemical component of blood substitutes because of too high a vapor pressure they can be used in perfluorochemical mixture which consists of less than 10% by volume of $C_8$ compounds and more than 90% by volume of $C_9$-$C_{11}$ compounds.

The present invention offers a novel liquid-phase perfluorination, which is easily controlled, safely manipulated, suitable for commercial scale-up, and particularly suited to completing the perfluorination of both the partially fluorinated ether and tert-amine derivatives.

The key points in operation of the present process are as follows:

a) the perfluorination is carried out at $-75°$ C. to $100°$ C., preferably $-30°$ to $25°$ C., in an inert liquid medium; preferably a perfluorochemical which may be the reaction product itself;

b) molecular fluorine itself, that is, undiluted $F_2$ is used as perfluorinating agent;

c) the $F_2$ is maintained in stoichiometric excess at all times during the reaction, so that the intermediate carbon radicals react with $F_2$ rather than each other;

d) the compound to be perfluorinated is metered and charged in slowly with vigorous stirring, so that it is rapidly diluted by the solvent and its concentration is kept low compared to $F_2$, and so that efficient heat dispersal occurs; and preferably;

e) UV irradiation, preferably of wavelength 20 to 330 nm is used to initiate fluorine atoms chains if spontaneous initiation is not sufficiently rapid, and further preferably.

The reaction is preferably carried out by employing UV illumination, to give smoothly the corresponding perfluorinated compounds in high yield. The partially fluorinated compounds as intermediates can be converted into the perfluorochemicals of formula [I] much smoother as compared to perfluorination of fluorine-free materials, and provides by-products in much smaller amount than the cobalt trifluoride fluorination or the gas phase fluorination.

This invention thus, produces perfluorinated ethers or tert-amines having 8-11 carbon atoms and preferably highly branched chain(s). They have high oxygen solubility, and a vapor pressure which is just about right for use in the body without adverse effects thereon. The emulsions prepared from the perfluoro derivatives thereof possess high stability, low body tissue residue.

Preparation of the partially fluorinated compounds

The partially fluorinated compounds of the formula [IV] to be perfluorinated are synthesized according to general reactions whose mechanisms are described in R. D. Chambers, "Fluorine in Organic Chemistry", N.Y. 1973. Fluorinated olefins such as hexafluoropropene dimer, hexafluoropropene trimer and tetrafluoroethylene pentamer which are easily available and have bulky skeletons are preferably used as starting materials for preparing the partially fluorinated compounds of the formula [IV]. The fluorinated olefins are reacted with alkyl-bearing nucleophilic agents or electrophilic agents. They react with monohydric alcohols as the agent in the presence of a base to give alkoxy substituent and occasionally hydrogen and fluoride ions, respectively, derived from HF liberated in the reaction, to form the partially fluorinated ether of the formula [IV].

For example, in case of the reaction between hexafluoropropene dimer and n-propyl alcohol the reaction is shown below:

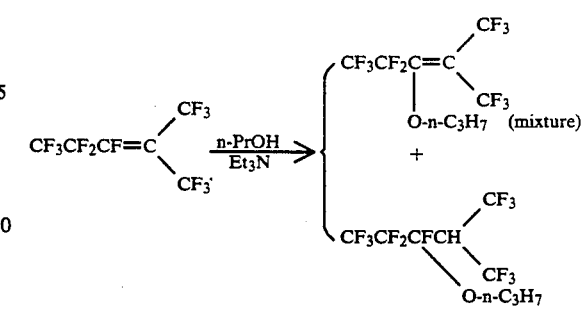

The olefins react with alkali metal alcoholates to form the objective ether.

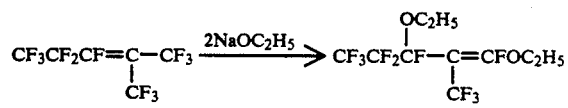

The partially fluorinated amines of the formula [IV] are also prepared by the reaction of the fluorinated olefins with dialkylamines in an appropriate solvent.

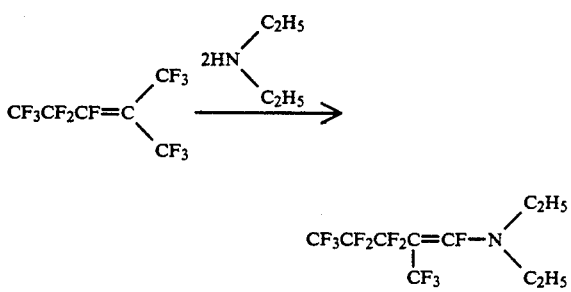

Also, the reaction of bis[dialkylamino] methanes in place of the dialkylamines gives the objective amines.

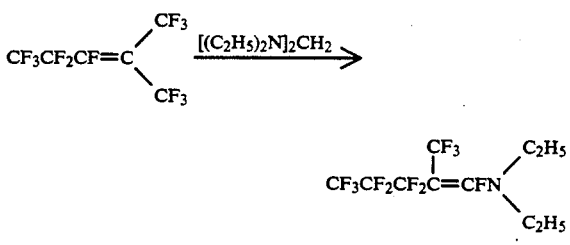

Bis[dialkylamino]methanes further react with the olefins in the presence of KF and acetylchloride to give a partially fluorinated tert-amine having one more carbon atom,

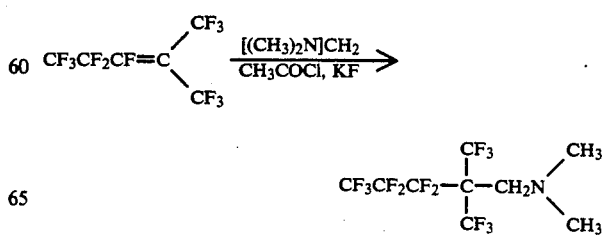

and in the presence of $Et_3N.BF_3$ or $Et_2O.BF_3$.

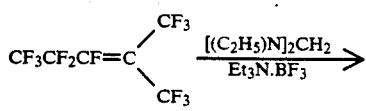

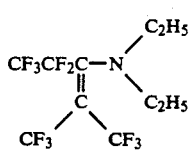

On the other hand, fluorinated alcohols react with alkyl-bearing electrophilic agents such as alkyl iodides to form the objective ethers.

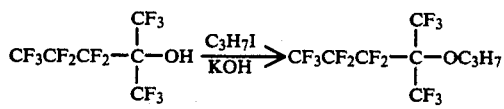

Hexafluoroacetone undergoes addition with alcohol, followed by alkylation at oxygen with alkyl iodides in the presence of a base to afford partially fluorinated ketals.

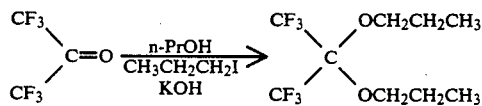

Also, fluorinated ketone reacts with dialkyl sulfate to form partially fluorinated alkylene ether.

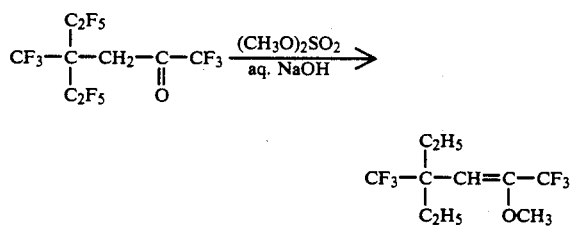

The objective partially fluorinated tertiary amines can also be prepared by reacting partially fluorinated or perfluoroalkylamines with alkyl trifluoromethanesulfonates.

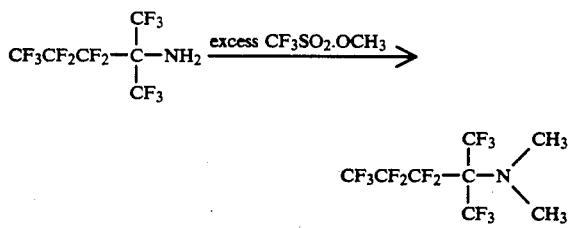

Preparation of the perfluorochemicals

The partially fluorinated ether or amine of the formula [IV] can be directly perfluorinated with molecular fluorine without dilution with any inert gas in an inert solvent. A typical perfluorination was started by filling the reaction chamber 1 with ca. 750 ml of an inert solvent, preferably perfluorinated-n-hexane or perfluorinated-isohexane, then flushing with ca. 50 ml/min $N_2$ for 30 min, and then cooling the condenser 2 and the reactor if necessary with an ice-bath 9 or a dry ice/dichloromethane bath 9 while flushing part 6 with nitrogen. After saturating the solvent with undiluted $F_2$ under UV irradiation 5, a starting material was metered at a rate of 1.0–20 ml/hr into the solvent kept saturated with $F_2$. The feeding rate definitely depends on the reaction scale, the amount of solvent used, the reactivity and hydrogen content of the material being fluorinated, and the light intensity. The $F_2$ amount to be fed is always kept in excess of the theoretically required amount. The reaction was continued until no consumption was observed ($F_2$ out = $F_2$ in). When the process is to be stopped, the feed of starting material is shut off, but fluorination is continued until $F_2$ is no longer consumed. The reaction was ended by flushing with $N_2$ for 1 hr, while keeping the reaction chamber cool, to expell unreacted $F_2$ and produced HF, and letting the reaction mixture be drained from pipe 10. The reaction mixture was washed and aqueous alkaline solution, then dried over KOH, and distilled to give a solvent fraction and product fractions.

The present invention is further illustrated by the following Examples which should not be construed to limit the invention thereto.

EXAMPLE 1

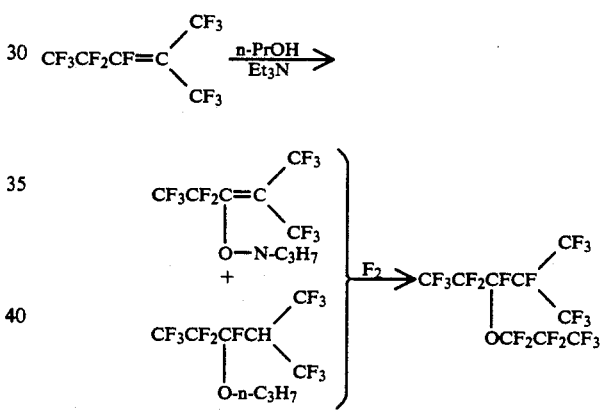

To a mixture of perfluoro-2-methyl-2-pentene (292.7 g, 0.98 mol) and n-propyl alcohol (59.0 g, 0.98 mol) was added dropwise triethylamine (101.2 g, 1.00 mol) over a 6-hour period at 0°–5° C. The entire mixture was stirred at room temperature overnight and poured into 300 ml of iced water. An oily lower phase which separated wash washed with dilute HCl and then with water, and dried over $CaCl_2$. Distillation of the lower phase at atmospheric pressure gave colorless liquid, bp 123°–135° C. (308 g), which appeared to be a mixture as shown above by nmr.

The mixture of partially fluorinated ethers (3-n-propoxy undecafluoro-2-methyl-2-pentene) and 2 H-3-n-propoxy dodecafluoro-2-methylpentane (ca. 8:2) (50 g) was pumped with vigorous stirring at a rate of 0.7 g/hr at 0° to 5° C. into a reactor containing 250 ml of perfluoro isohexane ($CF_3CF_2CF_2CF_2(CF_3)_2$) kept saturated with undiluted $F_2$ and irradiated through a sapphire window with a 100 w. medium-pressure Hg arc. The $F_2$ rate was 25±5 ml/min, which maintained a large excess over the theoretically required amount. After feeding all of the starting material, undiluted $F_2$ was continued with stirring for 5 hr while the reaction mixture was let warm slowly to room temperature. The reaction mixture was flushed with nitrogen for 30 min, then poured into aqueous alkaline solution, and shaken. A lower layer separated was heated to reflux temperature with 50 ml of diethylamine overnight, then treated with concentrated $H_2SO_4$, washed with water, and dried over $CaCl_2$. The fluorochemical layer was distilled at atmospheric pressure to give both perfluoroisohexane and of perfluoro-3-n-propoxy-2-methylpentane of 99% purity, confirmed by GC/MS and $^{19}F$-nmr, 42 g, b.p. 119°–121° C., d 1.73, vapor pressure 29 mmHG at 38° C.

EXAMPLES 2–6

Example 1 was repeated, provided that in place of n-propyl alcohol, isopropyl alcohol (Example 2), n-butyl alcohol (Example 3), isobutyl alcohol (Example 4), sec.butyl alcohol (Example 5) and isopentyl alcohol (Example 6) were respectively used in same moles.

Products are shown below:

| Ex. 2 Perfluroo-3-isopropoxy-2-methylpentane | |
|---|---|
| b.p. | 119°–120° C. |
| Vapor pressure (at 37.5° C.) | 35–36 mmHg |
| Molecular formula | $C_9F_{20}O$ |
| Chemical structure | $CF_3CF_2-CFCF(CF_3)_2$ <br> $\quad\quad\quad\quad\quad\quad\;\; |$ <br> $\quad\quad\quad\quad\quad\quad OCF(CF_3)_2$ |
| Yield | 58% |
| Ex. 3 Perfluoro-3-n-butoxy-2-methylpentane | |
| b.p. | 138°–140° C. |
| Vapor pressure (at 37.5° C.) | 11–13 mmHg |
| Molecular formula | $C_{10}F_{22}O$ |
| Chemical structure | $CF_3CF_2-CFCF(CF_3)_2$ <br> $\quad\quad\quad\quad\quad\quad\;\; |$ <br> $\quad\quad\quad\quad\quad\quad OCF_2CF_2CF_2CF_3$ |
| Yield | 80% |
| Ex. 4 Perfluoro-3-isobutoxy-2-methyl pentane | |
| b.p. | 136°–137° C. |
| Vapor pressure (at 37.5° C.) | 14–15 mmHg |
| Molecular formula | $C_{10}F_{22}O$ |
| Chemical structure | $CF_3CF_2-CFCF(CF_3)_2$ <br> $\quad\quad\quad\quad\quad\quad\;\; |$ <br> $\quad\quad\quad\quad\quad\quad OCF_2CF(CF_3)_2$ |
| Yield | 62% |
| Ex. 5 Perfluoro-3-sec-butoxy-2-methylpentane | |
| b.p. | 136°–138° C. |
| Vapor pressure (at 37.5° C.) | 13–14 mmHg |
| Molecular formula | $C_{10}F_{22}O$ |
| Chemical structure | $CF_3CF_2-CFCF(CF_3)_2$ <br> $\quad\quad\quad\quad\quad\quad\;\; |$ <br> $\quad\quad\quad\quad\quad\quad O-CF(CF_3)CF_2CF_3$ |
| Yield | 49% |
| Ex. 6 Perfluoro-3-isopentoxy-2-methylpentane | |
| b.p. | 148°–150° C. |
| Vapor pressure (at 37.5° C.) | 8–9 mmHg |
| Molecular formula | $C_{12}F_{24}O$ |
| Chemical structure | $CF_3CF_2-CFCF(CF_3)_2$ <br> $\quad\quad\quad\quad\quad\quad\;\; |$ <br> $\quad\quad\quad\quad\quad\quad OCF_2CF_2CF(CF_3)_2$ |
| Yield | 55% |

EXAMPLE 7

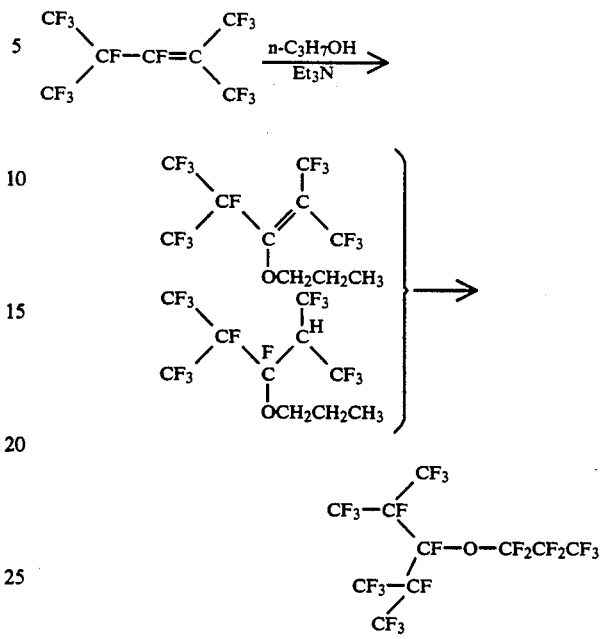

In accordance with the procedure of Example 1, a solution of triethylamine (50 g, 0.49 mol) in n-propyl alcohol (150 ml) was added with stirring to a mixture of perfluoro 2,4-dimethyl-2-pentene (168 g, 0.48 mol) and n-propyl alcohol (150 ml) over a 3 hr. period at 5°–10 C. The entire mixture was allowed to stir at room temperature for one week, poured into iced water, then washed with dilute HCl and with water, and dried over $CaCl_2$. An $^{19}F$-nmr of the product showed to be a mixture of two kinds of partially fluorinated ethers as shown above, b.p. 136°–142° C., 180 g.

In accordance with the procedure of Example 1, the partially fluorinated ethers, (50 g), 3-n-propoxytridecafluoro-2,4-dimethyl-2-pentane and 2-H-3-propoxytetradecafluoro-2,4-dimethylpentane (approx. 1:2), was pumped at a rate of 0.4 g/hr at 0° to 5° C. into a reactor containing $i$-$C_6F_{14}$ (perfluoroisohexane) kept saturated with undiluted $F_2$ under UV irradiation. When gas chromatographic analysis of the reaction mixture shown that the product contained 95% perfluoro-ether, confirmed by GC/MS, the fluorination was stopped. Distillation of the crude product, treated with base in accordance with the procedure of Example 1, gave 48 g of pure 3-n-propoxy-2,4-dimethylpentane, b.p. 134°–136° C., d 1.78, vapor pressure at 38° C.: 16–17 mmHg.

EXAMPLES 8–11

Example 7 repeated, provided that in place of n-propyl alcohol, ethyl alcohol (Example 8), isopropyl alcohol (Example 9), n-butyl alcohol (Example 10) and isobutyl alcohol (Example 11) were respectively used in same molar amounts. products are shown below:

| Ex. 8 Perfluoro-3-ethoxy-2,4-dimethylpentane | |
|---|---|
| b.p. | 118°–119° C. |
| Vapor pressure | 30–31 mmHg/38° C. |
| Molecular formula | $C_9F_{20}O$ |

-continued

| Chemical structure | (CF$_3$)$_2$CF—CFCF(CF$_3$)$_2$<br>                               |<br>                               OC$_2$F$_5$ |
|---|---|
| Yield | 92% |

Ex. 9 Perfluoro-3-isopropoxy-2,4-dimethylpentane

| b.p. | 133°–134° C. |
|---|---|
| Vapor pressure | 17–18 mmHg/38° C. |
| Molecular formula | C$_{10}$F$_{22}$O |
| Chemical structure | (CF$_3$)$_2$CF—CFCF(CF$_3$)$_2$<br>                                 |<br>                               OCF(CF$_3$)$_2$ |
| Yield | 61% |

Ex. 10 Perfluoro-3-n-butoxy-2,4-dimethylpentane

| b.p. | 150°–151° C. |
|---|---|
| Vapor pressure | 8–9 mmHg/38° C. |
| Molecular formula | C$_{11}$F$_{24}$O |
| Chemical structure | (CF$_3$)$_2$CF—CFCF(CF$_3$)$_2$<br>                                 |<br>                               OCF$_2$CF$_2$CF$_2$CF$_3$ |
| Yield | 77% |

Ex. 11 Perfluoro-3-isobutoxy-2,4-dimethylpentane

| b.p. | 149°–150° C. |
|---|---|
| Vapor pressure | 8–9 mmHg/38° C. |
| Molecular formula | C$_{11}$F$_{24}$O |
| Chemical structure | (CF$_3$)$_2$CF—CFCF(CF$_3$)$_2$<br>                                 |<br>                               OCF$_2$CF(CF$_3$)$_2$ |
| Yield | 53% |

Example 12

$$CF_3CF_2CF_2-\underset{\underset{CF_3}{|}}{\overset{\overset{CF_3}{|}}{C}}-OH \xrightarrow[\text{in DMSO}]{CH_3CH_2CH_2I,\ KOH}$$

$$CF_3CF_2CF_2(CF_3)_2C-O-CH_2CH_2CH_3 \xrightarrow{F_2}$$

C$_9$F$_{13}$H$_7$O $$CF_3CF_2CF_2-\underset{\underset{CF_3}{|}}{\overset{\overset{CF_3}{|}}{C}}-O-CF_2CF_2CF_3$$

C$_9$F$_{20}$O

Dimethylsulfoxide, 50 ml; perfluoro-2-methyl-2-pentanol, 12.5 g (0.0372 mol); KOH pellets (85%), 5.9 g (0.089 mol); and 1-isopropane, 8.5 g (0.05 mol) were combined and stirred at room temperature for 3 days. The reaction mixture was poured into 150 ml of water. The lower layer separated was dried over solid potassium hydroxide. Distillation of the crude product at atmospheric pressure gave 12 g of partially fluorinated ether (85%), 2-n-propoxy-tridecafluoro-2-methylpentane, b.p. 125° C.

In accordance with the procedures of Example 1, partially fluorinated ether (10 g) was metered at a rate of 1.5 g/hr at −30°±5° C. into the reaction containing perfluoroisohexane, kept saturated with undiluted F$_2$ with vigorous stirring under UV irradiation. The crude product, which weighed 11.2 g was analyzed by gas chromatography and showed to be >95% perfluoro ether. The mixture was then separated in accordance with the procedure of Example 1 to yield pure perfluoro ether, 9.8 g, b.p. 115°–116° C., d 1.70, vapor pressure at 38° C.: 33 mmHg.

EXAMPLES 13–17

Example 12 was repeated, provided that in place of 1-iodopropane, 2-iodopropane (Example 13), 1-iodobutane (Example 14), 1-iodo-2-methylpropane (Example 15), 2-iodobutane (Example 16) and 1-iodo-3-methylbutane (Example 17) were respectively used in the same molar amounts. Products are shown below.

Ex. 13 Perfluoro-2-isopropoxy-2-methylpentane

| b.p. | 120°–121° C. |
|---|---|
| Vapor pressure | 29–30 mmHg/38° C. |
| Molecular formula | C$_9$F$_{20}$O |
| Chemical structure | 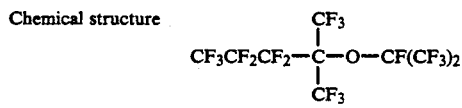 |
| Yield | 48% |

Ex. 14 Perfluoro-2-n-butoxy-2-methylpentane

| b.p. | 134°–136° C. |
|---|---|
| Vapor pressure | 13–14 mmHg/38° C. |
| Molecular formula | C$_{10}$F$_{22}$O |
| Chemical structure | 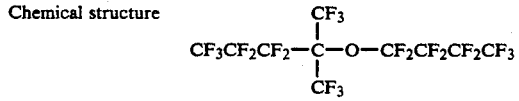 |
| Yield | 77% |

Ex. 15 Perfluoro-2-isobutoxy-2-methylpentane

| b.p. | 133°–134° C. |
|---|---|
| Vapor pressure | 15–16 mmHg/38° C. |
| Molecular formula | C$_{10}$F$_{22}$O |
| Chemical structure | 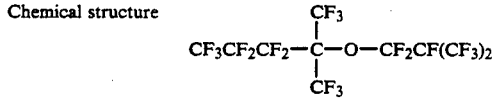 |
| Yield | 59% |

Ex. 16 Perfluoro-2-sec-butoxy-2-methylpentane

| b.p. | 133°–134° C. |
|---|---|
| Vapor pressure | 15–16 mmHg/38° C. |
| Molecular formula | C$_{10}$F$_{22}$O |
| Chemical structure | 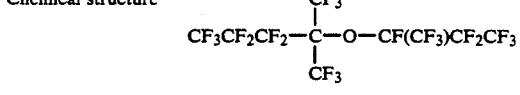 |
| Yield | 41% |

Ex. 17 Perfluoro-2-isovaleroxy-2-methylpentane

| b.p. | 146°–147° C. |
|---|---|
| Vapor pressure | 9–10 mmHg/38° C. |
| Molecular formula | C$_{11}$F$_{24}$O |
| Chemical structure | 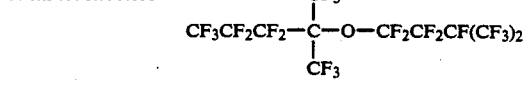 |
| Yield | 80% |

Example 18

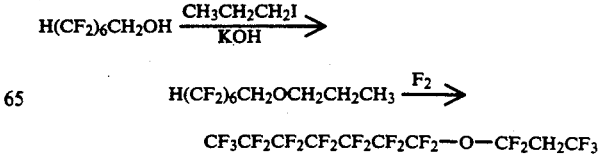

To a solution of 1H,1H,7H-dodecafluoro-1-heptanol (33.2 g, 0.10 mol), and KOH pellets (85%) (6.6 g, 0.12 mol) in 50 ml of dimethyl sulfoxide was added dropwise 1-iodopropane (20.4 g, 0.12 mol) at 5°–10° C. over a period of 30 min. After 24 hr. stirring, additional 1-iodopropane (10.2 g) and KOH (85%) (3.3 g) were added to the reaction mixture. The entire mixture was stirred at room temperature for 24 hr., then poured into 200 ml of iced water. The lower layer which separated was washed with water, then dried over solid potassium hydroxide. Distillation of the crude product at atmospheric pressure gave 29.7 g of partially fluorinated ether, b.p. 171°–172° C.

In accordance with the procedure of Example 1, the partially fluorinated ether (10 g) was metered at a rate of 1.0 g/hr at room temperature into a reactor containing perfluoro-n-hexane kept saturate with undiluted $F_2$ with vigorous stirring under UV irradiation. The crude product was treated with aqueous alkaline solution and with diethylamine and distilled to give pure perfluoroether, 11.3 g, b.p. 136°–137° C., b 1.76, vapor pressure at 38° C.: 15–16 mmHg.

Examples 19–23

Example 18 was repeated, provided that in place of 1-iodopropane, iodoethane (Example 19), 2-iodopropane (Example 20), 1-iodobutane (Example 21), 1-iodo-2-methylpropane (Example 22) and 2-iodobutane (Example 23) were respectively used.

Products are shown below:

| Ex. 19 Perfluoro-1-ethoxyheptane | |
|---|---|
| b.p. | 118°–119° C. |
| Vapor pressure | 33 mmHg/38° C. |
| Molecular formula | $C_9F_{20}O$ |
| Chemical structure | $CF_3(CF_2)_5CF_2-O-C_2F_5$ |
| Yield | 90% |
| Ex. 20 Perfluoro-1-isopropoxyheptane | |
| b.p. | 136°–137° C. |
| Vapor pressure | 14–15 mmHg/38° C. |
| Molecular formula | $C_{10}F_{22}O$ |
| Chemical structure | $CF_3(CF_2)_5CF_2-O-CF(CF_3)_2$ |
| Yield | 76% |
| Ex. 21 Perfluoro-1-n-butoxyheptane | |
| b.p. | 150°–151° C. |
| Vapor pressure | 8–9 mmHg/38° C. |
| Molecular formula | $C_{11}F_{24}O$ |
| Chemical structure | $CF_3(CF_2)_5CF_2-O-CF_2CF_2CF_2CF_2CF_3$ |
| Yield | 86% |
| Ex. 22 Perfluoro-1-isobutoxyheptane | |
| b.p. | 149°–150° C. |
| Vapor pressure | 8–9 mmHg/38° C. |
| Molecular formula | $C_{11}F_{24}O$ |
| Chemical structure | $CF_3(CF_2)_5CF_2-O-CF_2CF_2(CF_3)_2$ |
| Yield | 88% |
| Ex. 23 Perfluoro-1-sec-butoxyheptane | |
| b.p. | 146°–147° C. |
| Vapor pressure | 9–10 mmHg/38° C. |
| Molecular formula | $C_{11}F_{24}O$ |
| Chemical structure | $CF_3(CF_2)_5CF_2-O-CF(CF_3)CF_2CF_3$ |
| Yield | 79% |

Example 24

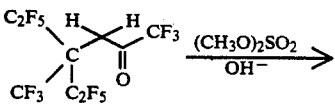

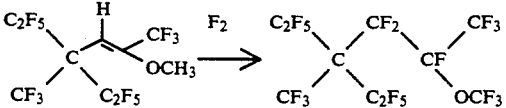

3H,3H-hexadecafluoro-4-ethyl-4-methyl-2-hexanone, which was prepared by the reaction of tetrafluoroethylene pentamer with aqueous NaOH followed by acidification of the reaction product, 43 g (0.1 mol); 1.2 M KOH, 100 ml; and dimethyl sulfate, 13 g (0.1 mol) were combined and stirred at room temperature for 18 hr. At the end of the reaction period a lower layer which formed was separated, washed with aqueous alkaline solution and with saturated NaCl, then dried over $CaCl_2$, and distilled to give the ether, b.p. 136.5°–137° C., 30.2 g, the structure of which is confirmed by $^{19}F$ nmr.

In accordance with the procedure of Example 1, the reactants were fluorinated to obtain perfluoro-2-methoxy-4-ethyl-4-methylhexane.

| b.p. | 133°–124° C. |
|---|---|
| Vapor pressure | 17–18 mmHg/38° C. |
| Molecular formula | $C_{10}F_{22}O$ |
| Chemical structure | $CF_3(C_2F_5)_2CCF_2CF-CF_3$<br>$\quad\quad\quad\quad\quad\quad\quad\quad\ \ |$<br>$\quad\quad\quad\quad\quad\quad\quad\quad\ \ OCF_3$ |
| Yield | 62% |

EXAMPLE 25

Example 24 was repeated, provided that in place of dimethyl sulfate, diethyl sulfate was used to obtain perfluoro-2-ethoxy-4-ethyl-4-methylhexane.

| b.p. | 151°–152° C. |
|---|---|
| Vapor pressure | 8–9 mmHg/38° C. |
| Molecular formula | $C_{11}F_{24}O$ |
| Chemical structure | $CF_3(C_2F_5)_2CCF_2CFCF_3$<br>$\quad\quad\quad\quad\quad\quad\quad\quad\ \ |$<br>$\quad\quad\quad\quad\quad\quad\quad\quad\ \ OC_2F_5$ |
| Yield | 55% |

EXAMPLE 26

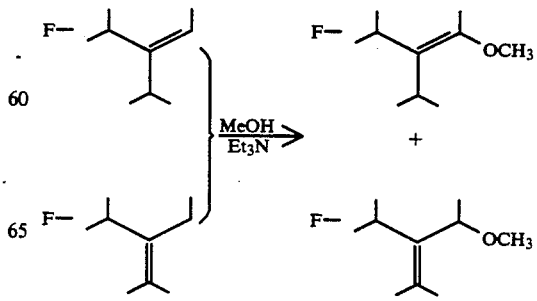

-continued

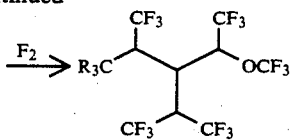

A solution of triethylamine (11.4 g, 0.11 mol) in methanol (40 ml) was added dropwise at room temperature to a stirred mixture of hexafluoropropane trimer (isomer mixtures), 51.8 g, 0.115 mol, and methanol (30 ml) over a period of 30 minutes. The entire mixture was then heated to reflux for 1 hour, and then poured into 120 ml of cold 1N HCl. The lower layer of the reaction mixture was washed with saturated NaCl solution, dried over $CaCl_2$, and distilled to obtain 40.3 g of the products, bp 143°–144° C., which was a mixture (15:1) of double bond isomers, as confirmed by $^{19}F$ nmr and H nmr.

In accordance with the procedure of Example 1, the reactants were fluorinated to obtain perfluoro-2-methoxy-3-isopropyl-4-methylpentane.

| b.p. | 131°–132° C. |
|---|---|
| Vapor pressure | 18–19 mmHg/38° C. |
| Molecular formula | $C_{10}F_{22}O$ |
| Chemical structure | $(CF_3)_2CFCF(CF_3)$—O—$CF_3$ |
| | $\|$ |
| | $CF(CF_3)_2$ |
| Yield | 12% |

EXAMPLE 27

Example 26 was repeated, provided that in place of methyl alcohol, ethyl alcohol was used to obtain perfluoro-2-ethoxy-3-isopropyl-4-methylpentane.

| b.p. | 145°–146° C. |
|---|---|
| Vapor pressure | 10–11 mmHg/38° C. |
| Molecular formula | $C_{11}F_{24}O$ |
| Chemical structure | $(CF_3)_2CFCFCF(CF_3)$—O—$C_2F_5$ |
| | $\|$ |
| | $CF(CF_3)_2$ |
| Yield | 10% |

EXAMPLE 28

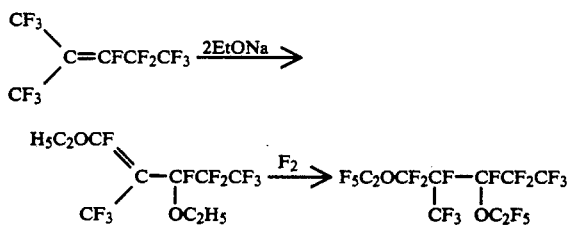

An ethanolic solution of sodium ethoxide (Na, 1.0 g in EtOH, 20 ml) was vigorously stirred into the perfluoro-2-methyl-2-pentene (6 g, 0.02 mol), the temperature being kept at −10° to 0° C. After 30 min of stirring at 0° C., the reaction mixture was poured into water. The resulting oily layer was separated, washed with water, and then refluxed with aqueous KOH (15%) for 16 hr. After washing and drying, and crude product was distilled in vacuo to give 1,3-diethoxy-decafluoro-2-methyl-1-pentene, bp. 81°–82° C./20 mmHg, 3.5 g.

Perfluorination, in accordance with the procedure of Example 1, of 1,3-diethoxy-decafluoro-2-methyl-1-pentene gave perfluoro-1,3-diethoxy-2-methylpentane in 86% yield, bp 134°–136° C., d 1.82, vapor pressure at 38° C.: 13–14 mmHg.

EXAMPLE 29

Example 28 was repeated, provided that in stead of sodium ethoxide, sodium methoxide was used to obtain perfluoro-1,3-dimethoxy-2-methylpentane.

| b.p. | 105°–106° C. |
|---|---|
| Vapor pressure | 48–50 mmHg/38° C. |
| Molecular formula | $C_8F_{18}O_2$ |
| Chemical structure | $F_3COCF_2CF$—$CF$—$CF_2CF_3$ |
| | $\|$  $\|$ |
| | $CF_3$  $OCF_3$ |
| Yield | 95% |

EXAMPLE 30

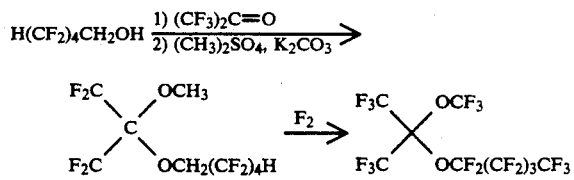

Hexafluoroacetone (22 ml at −78° C., 0.21 mol) was slowly distilled into a stirred solution of 48.9 g (0.21 mol) of 1H,1H,5H-octafluoro-1-pentanol in 50 ml of acetonitrile. The entire mixture was stirred at room temperature overnight. The resulting hemiketal was treated with 29.3 g (0.23 mol) of dimethyl sulfate followed by 24 g of potassium carbonate added in small portions over one hour, and the mixture was stirred overnight, and poured into 100 ml of water. The lower layer was separated, washed with aqueous alkali and then water, and dried over $CaCl_2$. Distillation gave 40 g (46%) of ketal as a colorless liquid: bp 155°–156° C.

The ketal (10 g) was fluorinated in accordance with the procedure of Example 1, to give perfluoro-2-pentoxy-2-methoxypropane, 9.1 g, bp 123°–124° C., d 1.80, vapor pressure at 38° C.: 28–29 mmHg.

EXAMPLE 31

Example 30 was repeated, using diethylsulfate in place of dimethyl sulfate to obtain perfluoro-2-pentoxy-2-ethoxy propane.

| b.p. | 135°–136° C. |
|---|---|
| Vapor pressure | 13–14 mmHg/38° C. |
| Molecular formula | $C_{10}F_{22}O_2$ |
| Chemical structure | $CF_3$  O—$CF_2CF_3$ |
| | \ / |
| | C |
| | / \ |
| | $CF_3$  O—$CF_2CF_2CF_2CF_3$ |
| Yield | 75% |

EXAMPLE 32

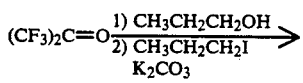

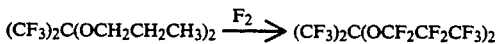

Hexafluoroaceteone, 16.6 g (0.1 mol) was slowly distilled into a three necked flask cooled by a dry ice/isopropanol bath and equipped with a dry ice/isopropaneol condenser, dropping funnel and nitrogen gas inlet. To the stirred hexafluoroacetone was added propyl alcohol (35 g) in portions at $-75°$ C. The entire mixture was let warm slowly to ambient temperature and kept stirring until hexafluoroacetone no longer refluxed from the condenser. Ten grams of $K_2CO_3$ was placed in the pot containing the hemi-ketal formed, and propyl iodide, 17 g (0.1 mol) was added to the mixture over one hour. The whole was stirred at room temperature overnight, poured into iced water, and extracted with diethyl ether. The dried ether extract was concentrated and distilled to give 8 g of the corresponding ketal, 2,2-di-n-propoxy-hexafluoropropane.

The ketal was perfluorinated according to the procedure of Example 1 to obtain perfluoro-2,2-di-n-propoxypropane, b.p. $117°-118°$ C., d 1.81, vapor pressure at $38°$ C.: 29–30 mmHg.

EXAMPLE 33

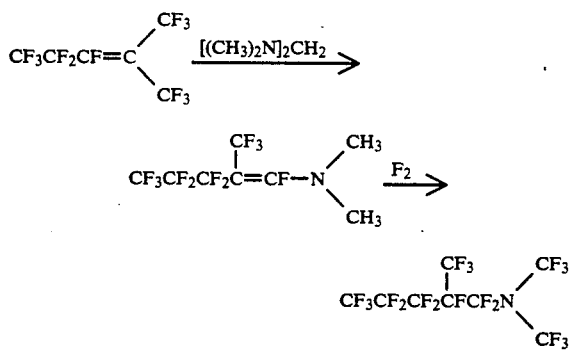

Perfluoro-2-methyl-2-pentene, 5.0 g (0.017 mol); 10 ml of dry dimethylformamide (DMF); and bis(dimethylamino)-methane, 1.75 g (0.017 mol), were placed in a flask, which was closed with a drying tube, in that order, then stirred at room temperature for 2 hours, and poured into 30 ml of iced water. A lower layer of the reaction mixture was washed quickly with saturated NaCl solution and dried over $CaCl_2$; and $^{19}F$ nmr spectrum of this phase indicated it to be partially fluorinated enamine of about 98% purity. A double bond isomer, perfluoro-2-methyl-3-pentene, $CF_3CF=CFCF(CF_3)_2$, can be substituted for the dimer being used in this case.

The enamine was subjected to perfluorination without further purification as soon as possible in accordance with the procedure of Example 1. The enamine 24 g, was pumped at a rate of 0.3 g/hr at room temperature into stirred 400 g of perfluoroisohexane kept saturated with undiluted $F_2$ under UV irradiation. After addition the reaction mixture was flushed with pure nitrogen for 1 hr., then treated with aqueous KOH, dried over $CaCl_2$, and distilled to give both perfluoroisohexane and 24 g of perfluoro-1-dimethylamino-2-methylpentane of at least 99% purity by gas chromatography and $^{19}F$-nmr, b.p. $110°-11°$ C., d 1.84, vapor pressure at $38°$ C.: 37–38 mmHg.

EXAMPLE 34

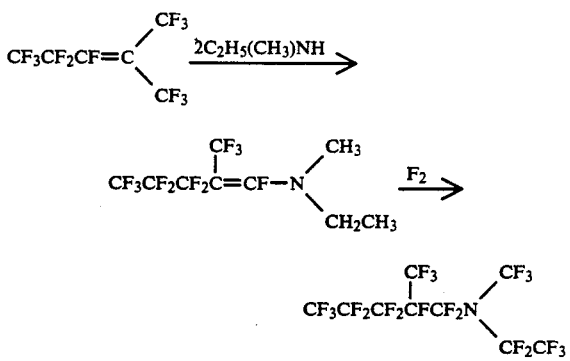

To stirred perfluoro-2-methyl-2-pentene (30.3 g) was added dropwise ethylmethylamine (10.6 g) under ice-water cooling, and the entire mixture was allowed to stir at room temperature overnight. The reaction mixture was poured into iced water. A lower layer which formed was washed with diluted HCl and then water, and dried over $MgSO_4$. Both $^{19}F$ and $^1H$ nmr spectra of this layer indicated it to be a fluorinated enamine with at least 95% purity. Distillation gave a yellow liquid (25.2 g), bp $88°$ C./21 mmHg.

The enamine was treated with a solvent to be used for fluorination to remove insoluble materials prior to fluorination, and then subjected to fluorination as soon as possible in accordance with the procedure of Example 1, giving perfluoro-1-ethylmethylamino-2-methylpentane in 75% yield, bp $128°-129°$ C., d 1.84, vapor pressure at $38°$ C.: 21 mmHg.

EXAMPLE 35

Example 34 was repeated, provided that in place of ethylmethylamine, diethylamine was used to obtain perfluoro-1-diethylamino-2-methylpentane.

| | |
|---|---|
| b.p. | $147°-148°$ C. |
| Vapor pressure | 8–9 mmHg/$38°$ C. |
| Molecular formula | $C_{10}F_{23}N$ |
| Chemical structure | $CF_3CF_2CF_2CFCF_2N(C_2F_5)_2$<br>$\quad\quad\quad\quad\quad\;\; \mid$<br>$\quad\quad\quad\quad\quad\;\; CF_3$ |
| Yield | 88% |

EXAMPLE 36

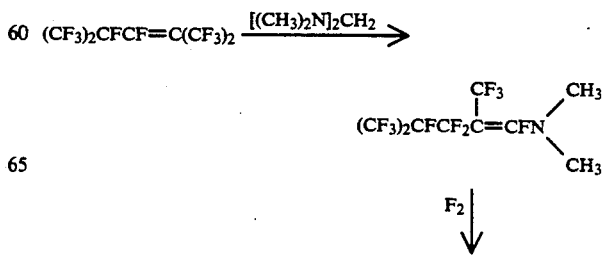

-continued

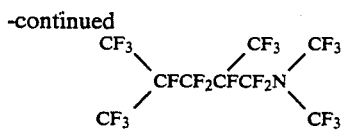

In accordance with the procedure of Example 33 perfluorinated-2,4-dimethyl pentane, 20 g (0.057 mol), 50 ml of dry DMF, and bis[dimethylamino]methane, 6 g (0.59 mol) were placed in a flask, then stirred at room temperature for 2 hr., and poured into 100 ml of iced water. A lower layer was washed with saturated NaCl and dried over CaCl$_2$. Distillation give a yellow liquid (16.9 g), b.p. 90°-92° C./25 mmHg.

The enamine, 15 g was successfully fluorinated following the procedure of Example 1, to yield perfluorotertiary-C$_9$-amine in high yield. b.p. 128°-129° C., d 1.85, vapor pressure at 38° C.: 18-19 mmHg.

EXAMPLE 37

Example 34 was repeated exactly, provided that in place of perfluoro-2-methyl-2-pentene, perfluoro-2,3-dimethyl-2-pentene was used to obtain perfluoro-1-ethylmethylamino-2,4-dimethylpentane.

| | |
|---|---|
| b.p. | 143°-144° C. |
| Vapor pressure | 12-13 mmHg/38° C. |
| Molecular formula | C$_{10}$F$_{23}$N |
| Chemical structure | (CF$_3$)$_2$CFCF$_2$CF(CF$_3$)CF$_2$N(CF$_3$)C$_2$F$_5$ |
| Yield | 60% |

EXAMPLE 38

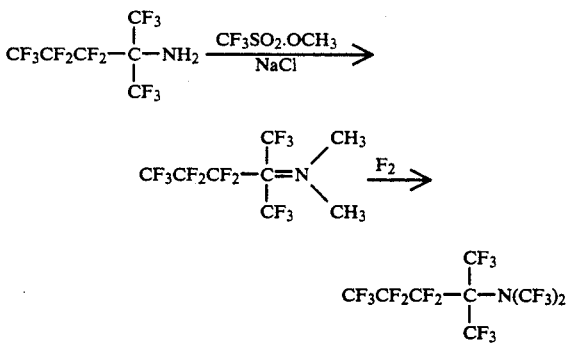

Distilled 2-amino-tridecafluoro-2-methylpentane, 6.7 g (0.020 mol), and freshly prepared methyltrifluoromethane sulfonate, 7.2 g (0.044 mol), were placed in a 100 ml flask equipped with a reflux condenser and drying tube. An F-nmr spectrum of the reaction mixture after heating to 80° C. for 24 hr. showed that all of the starting material was converted to secondary amine (approx. 70%) and tertiary amine. A further 3.6 g (0.022 mol) of methyl triflate and 5 g of powdered sodium chloride were added to the mixture on the first day and again on the 3rd day of the reaction period, and the heating was continued for 5 days. The reaction mixture was then diluted with 150 ml of water and carefully made alkaline with 6M-KOH solution. The aqueous solution was stirred at room temperature overnight to decompose unreacted triflate. The lower layer which separated was washed with water, dried over CaCl$_2$ and distilled at atmospheric pressure to give 5.1 g (70%) of a partially fluorinated amine, 2-dimethylamino-tridecafluoro-2-methylpentane, b.p. 123°-124° C. The reactant was successfully fluorinated following the procedure of Example 1 to yield perfluoro-2-dimethylamino-2-methylpentane.

| | |
|---|---|
| b.p. | 109°-110° C. |
| Vapor pressure | 37-38 mmHg/38° C. |
| Molecular formula | C$_8$F$_{19}$N |
| Chemical structure | CF$_3$CF$_2$CF$_2$(CF$_3$)$_2$C—N(CF$_3$)$_2$ |
| Yield | 82% |

EXAMPLE 39

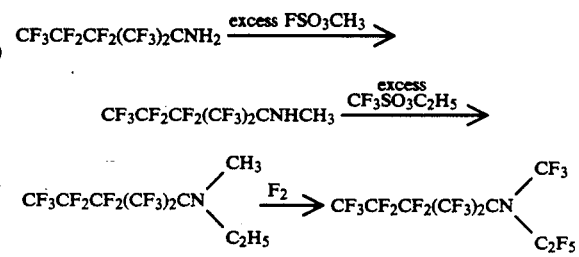

Distilled 2-amino-tridecafluoro-2-methylpentane, 67.0 g (0.20 mol), and freshly distilled methylfluorosulfonate, ca. 100 g (ca. 0.88 mol) were placed in a 250 ml flask with a glass stopper. After 5 weeks of standing at room temperature, the mixture was diluted with 500 ml of water and carefully made alkaline and aqueous KOH solution. A lower layer which separate was washed with aqueous alkali and then water, and dried over CaCl$_2$. Distillation gave a colorless liquid, bp. 108°-109° C., which was confirmed by $^{19}$F nmr and $^1$H nmr to be a mixture of 2-methylaminotridecafluoro-2-methylpentane and 2-dimethylaminotridecafluoro-2-methylpentane in a ratio of 97:3.

In accordance with the procedure of Example 38, a mixture of distilled 2-methylamino-trifluorodecane-2-methylpentane, 18.0 g (0.05 mol; calculated as 97% purity), freshly prepared ethyl trifluoromethanesulfonate, 35.6 g (0.20 mol), and powdered sodium chloride, 12 g, was heated to 80° C. for 1 week. The reaction mixture was then distilled with ice water and carefully made alkaline with aqueous KOH solution, and the whole was stirred at room temperature overnight. A lower layer which formed was washed with aqueous KOH solution and then water, dried over CaCl$_2$, and distilled to give a colorless liquid, 2-ethylmethylamino-tridecafluoro-2-methylpentane, bp 135°-136° C., 15.8 g, which was identified by $^{19}$F nmr and $^1$H and by IR.

The reactant was successfully perfluorinated following the procedure of Example 1 to afford tert-C$_9$-amine, Perfluoro-2-methylethylamino-2-methylpentane.

| | |
|---|---|
| b.p. | 127°-128° C. |
| Vapor pressure | 20-21 mmHg/38° C. |
| Molecular formula | C$_9$F$_{21}$N |
| Chemical structure | CF$_3$CF$_2$CF$_2$(CF$_3$)$_2$C—N(CF$_3$)(CF$_2$CF$_3$) |

EXAMPLE 40

Example 39 was repeated, provided that in place of ethyltrifluoromethane sulfonate, propyltrifluoromethane sulfonate was used to obtain perfluoro-2-methylpropylamino-2-methylpentane.

| b.p. | 145°–146° C. |
|---|---|
| Vapor pressure | 9–10 mmHg/38° C. |
| Molecular formula | $C_{10}F_{23}N$ |
| Chemical structure | 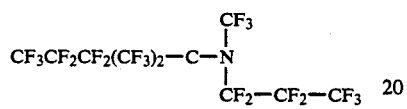 |

| Yield | 55% |
|---|---|

EXAMPLE 41

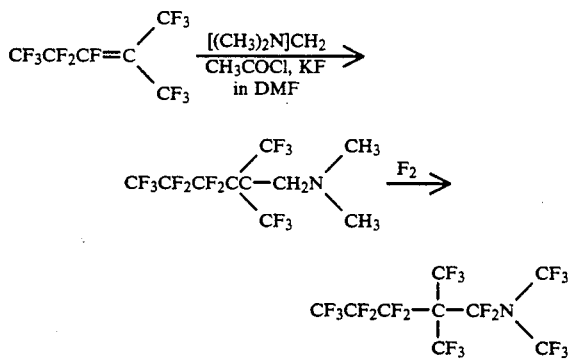

To a stirred solution of bid[dimethylamino]-methane, 10.0 g (0.098 mol) in 200 ml of dry diethyl ether, was added acetyl chloride, 8.0 g (0.102 mol) dropwise over a 15 minutes period at 10°–15° C. After one hour of stirring, the ethereal layer was removed while keeping moisture out. To the residue (dimethyl methylene immonium chloride) was added a mixture of dry KF, 10.0 g (0.172 mol), 70 ml of dried DMF, and perfluoro-2-methyl-2-pentene, 30 g (0.100 mol), in that order at −5° to 0° C. After stirring for one hour, the reaction mixture was filtered to remove solid, and then poured into iced water. A lower layer formed was washed with saturated NaCl quickly, and dried over $CaCl_2$. Both $^{19}F$-nmr and $^1H$-nmr of the layer showed to be a partially fluorinated amine, 1-dimethylamino-1H,1H-tridecafluoro-2-dimethylpentane, 23.3 g.

| b.p. | 62° C./1 mmHg |
|---|---|

The partially fluorinated amine, 15 g, was successfully fluorinated following the procedure of Example 1, to yield perfluoro tertiary $C_9$ amine in high yield. b.p. 130°–131° C., vapor pressure at 38° C.: 18–19 mmHg.

EXAMPLE 42

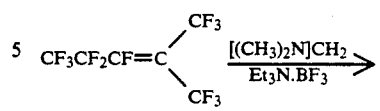

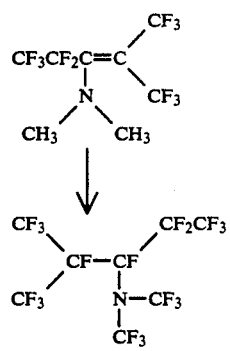

To a stirred solution of boron trifluoride etherate, etherate, 26 g (0.18 mol) in 300 ml of diethyl ether in a 3-neck flask equipped with a pressure equalizing funnel and drying tube, was added in succession: triethylamine 20.2 g (0.20 mol); perfluoro-2-methyl-2-pentene, 51.0 g (0.17 mol); and bis[dimethylamino]methane 17.9 g (0.175 mol). The entire mixture was stirred at room temperature for 2 days, and poured into 300 ml of iced water. The etheral layer was washed with water, then dried over $CaCl_2$, and the ether was removed at room temperature in vacuo. Distillation of the residue at low pressure gave an enamine, 3-dimethylamino-undecafluoro-2-methyl-2-pentene, 41 g, the structure of which was confirmed by $^{19}F$-nmr, b.p. 67°–69° C./3 mmHg.

The enamine, 15 g, was successfully fluorinated following the procedure of Example 1, to yield perfluorotertiary $C_8$ amine, 3-perfluoro-3-dimethylamino-2-methylpentane, in high yield, b.p. 110°–111° C. d 1.85, vapor pressure at 38° C.: 37–38 mmHg.

EXAMPLE 43

Example 42 was repeated, provided that in place of bis[dimethylamino]methane, bis[diethylamino]methane was used to obtain perfluoro-3-diethylamino-2-methylpentane.

| b.p. | 145°–147° C. |
|---|---|
| Vapor pressure | 9–10 mmHg/38° C. |
| Molecular formula | $C_{10}F_{23}N$ |
| Chemical structure | 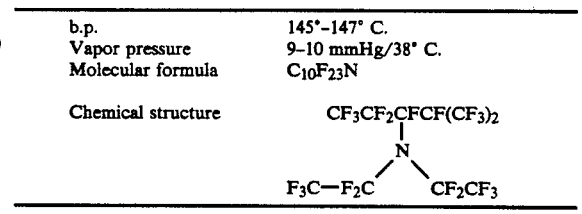 |

EXAMPLE 44

Example 42 was repeated, provided that in place of hexafluoropropene dimer, perfluoro-2,4-dimethyl-2-pentene was used to obtain perfluoro-3-dimethylamino-2,4-dimethylpentane.

| b.p. | 128°–129° C. |
|---|---|
| Vapor pressure | 21–22 mmHg/38° C. |
| Molecular formula | $C_9F_{21}N$ |

-continued

| Chemical structure | $(CF_3)_2CFCFCF(CF_3)_2$ |
| --- | --- |
| | $\quad\quad\quad\quad\quad\quad |$ |
| | $\quad\quad\quad\quad\quad\quad N$ |
| | $\quad\quad\quad\quad\quad/\quad\backslash$ |
| | $\quad\quad\quad\quad CF_3\quad CF_3$ |
| Yield | 79% |

Preparation of emulsion

The present perfluorochemicals can easily be emulsified into an emulsion stable even after sterilization with average particle size from about 0.16 to about 0.08μ, preferably according to the method of U.S. Pat. No. 4,252,827.

For instance, in 8 liters of distilled water, was dissolved 300 g of a polyoxyethylene-polyoxypropylene copolymer (average molecular weight: 8,350). To the solution were added 40 g of soybean phospholipids, 2 g of potassium oleate, and 3 kg of the present perfluorochemical. The resulting mixture was stirred in a mixer to form a crude emulsion. The resulting crude emulsion was charged into the liquid tank of a jet emulsion was charged into the liquid tank of a jet emulsifier (made by Manton-Gaulin Co.) and emulsified by passing it twelve times through a valve at a high pressure of 200 to 500 kg/cm², while maintaining the liquor temperature at 35±5° C., to effect emulsification. The resulting emulsion contained 30.5% (W/V) of perfluorocompound.

The average particle diameter after sterilization was 0.08 to 0.16μ depending on the kind of the perfluorochemicals, as measured by the centrifugal sedimentation method by K. Yokoyama et al. [Chem. Phar. Bull. (Tokyo) 22 (12), pages 2966–1971].

TEST EXAMPLES

According to the above preparation method of the emulsion, the emulsions of various perfluoroalkyl ether derivatives are prepared. Nine parts by volume of the resulting emulsion were diluted with 1 part by volume of an electrolyte solution of the following composition:

| NaCl | 6.0% (W/V) |
| --- | --- |
| NaHCO₃ | 2.1 |
| KCl | 0.336 |
| MgCl₂.6H₂O | 0.427 |
| CaCl₂.2H₂O | 0.356 |
| D-glucose | 1.802 |
| pH | 8.0 |

The emulsions were sterilized by heating at 100° C. for 30 minutes in a nitrogen atmosphere. The emulsions were used for the following test.

1) Stability

The emulsions were stored at 4° C. and the stability was measured in terms of the change of the particle size by the following measures.

| Excellent: | Particle size is hardly increased one month after the storage. |
| --- | --- |
| Good: | The increase of the particle size is at most 50% or liquid-particle separation is observed one month after the storage. |

2) Toxicity

The emulsions which had been made physiologically isotonic were injected intravenously to the wister male rates of 100 to 100 g. One week after the injection acute toxicity was observed by dissection, and evaluation was effected according to the following measures.

| Toxic: | Occurrence of pulmonary emphysema. LD₅₀: 2–4 g/kg |
| --- | --- |
| Non toxicic: | No occurence of pulmonary emphysema. LD₅₀: above 20 g/kg |

3) Elimination property

This property was measured by the half reduction term in the body of the rat, and evaluated as follows:

| Poor: | About 100 days |
| --- | --- |
| Fair: | Several ten days |

The tests were carried out with respect to the total carbon number, chemical structure and the presence of perfluoromethyl ether linkage of the perfluoroalkyl ether derivatives.

The results obtained are shown as follows:

| Item 1: Total carbon number | | | |
| --- | --- | --- | --- |
| Perfluoroalkyl ethers | | Stability | |
| Carbon number | Chemical Formula | of Emulsion | Toxicity |
| 9 | *F—C(CF₃)(CF₃)—O—CF₂CF₂CF₂CF₂CF₂CF₃ | Good | Toxic |
| 10 | CF₃CF₂CF₂—C(CF₃)(CF₃)—O—CF₂CF₂CF₂CF₃ | Excellent | Non toxic |

*Nichka's compound

| Item 2: Chemical structure (Branched chains) | | | | Stability | Elimination |
| --- | --- | --- | --- | --- | --- |
| | Perfluoroalky ethers | | | of | |
| Carbon number | | $X_1$ $X_2$ in the formula [II] | Chemical Formula | Emulsion | property |
| $C_{10}$ | Straight chain | F | $CF_2(CF_2)_6$—O—$CF_2CF_2CF_3$ | good | poor |
| | Branched chain | $(CF_3)_2CF$ F | $(CF_3)_2CF$<br>\|<br>$(CF_3)_2CF$—CF—O—$CF_2CF_2CF_3$ | excellent | fair |

| Item 3: The presence of perfluoromethyl ether linkage | | | Stability |
| --- | --- | --- | --- |
| | Perfluoroalkyl ethers | | |
| Carbon number | $R_{F2}$ in formula [II] | Chemical Formula | of Emulsion |
| $C_{10}$ | $CF_3$ | $CF_3$<br>\|<br>$(CF_3CF_2)_2CCF_2$—CF—$OCF_3$<br>\|<br>$CF_3$ | good |
| | $C_2F_5$ | $(CF_3)_2CF$<br>\|<br>$(CF_3)_2CF$—C—$OC_2F_5$<br>\|<br>$CF_3$ | excellent |

What is claimed is:

1. A perfluoroalkyl tertiary amine derivative of the formula

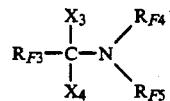

wherein $R_{F3}$ is $$C_3F_7CF—,\ C_3F_7—,\ CF_3CFCF_2CF—\ or\ CF_3CF—,$$
$$\quad\ \ |\qquad\qquad\qquad\ \ \ |\quad\ \ \ |\qquad\qquad\ \ \ |$$
$$\ \ CF_3\qquad\qquad\qquad CF_3\ CF_3\qquad\quad\ CF_3$$

$R_{F4}$ is $C_3F_7$ or $C_2F_5$, $R_{F5}$ is $C_2F_5$ or $CF_3$, $X_3$ is F and $X_4$ is $C_2F_5$, $CF_3$ or F, or $X_3$ and $X_4$ are together $CF_3$ when $R_{F3}$ is $C_3F_7$, and the total number of carbon atoms is 10.

2. A perfluoroalkyl tertiary amine derivative selected from the group consisting of:
   Perfluoro-1-diethylamino-2-methylpentane,
   Perfluoro-1-ethylmethylamino-2,4-dimethylpentane,
   Perfluoro-2-methylpropylamino-2-methylpentane, and
   Perfluoro-3-diethylamino-2-methylpentane.

* * * * *